US008440392B2

(12) United States Patent
Pamula et al.

(10) Patent No.: US 8,440,392 B2
(45) Date of Patent: May 14, 2013

(54) METHOD OF CONDUCTING A DROPLET BASED ENZYMATIC ASSAY

(75) Inventors: Vamsee K. Pamula, Durham, NC (US); Allen Eckhardt, Durham, NC (US); Jeremy Rouse, Raleigh, NC (US); Vijay Srinivasan, Durham, NC (US)

(73) Assignee: Advanced Liquid Logic Inc., Research Triangle Park, NC (US)

( * ) Notice: Subject to any disclaimer, the term of this patent is extended or adjusted under 35 U.S.C. 154(b) by 145 days.

(21) Appl. No.: 12/531,844

(22) PCT Filed: Mar. 23, 2008

(86) PCT No.: PCT/US2008/057959
§ 371 (c)(1),
(2), (4) Date: Feb. 26, 2010

(87) PCT Pub. No.: WO2008/116209
PCT Pub. Date: Sep. 25, 2008

(65) Prior Publication Data
US 2010/0151439 A1   Jun. 17, 2010

Related U.S. Application Data

(60) Provisional application No. 60/896,341, filed on Mar. 22, 2007.

(51) Int. Cl.
*C12Q 1/00* (2006.01)
(52) U.S. Cl.
USPC .................................................. 435/4; 347/68
(58) Field of Classification Search ......... 435/4; 347/68
See application file for complete search history.

(56) References Cited

U.S. PATENT DOCUMENTS

| | | | |
|---|---|---|---|
| 5,753,186 A | 5/1998 | Hanley et al. | |
| 6,171,810 B1 | 1/2001 | Zhu | |
| 6,294,063 B1 | 9/2001 | Becker et al. | |
| 6,406,667 B1* | 6/2002 | Singh et al. | 422/52 |
| 6,911,132 B2* | 6/2005 | Pamula et al. | 204/600 |
| 7,108,354 B2 | 9/2006 | Gulvin et al. | |
| 7,939,021 B2* | 5/2011 | Smith et al. | 422/68.1 |
| 2002/0102737 A1 | 8/2002 | Millington et al. | |
| 2003/0148538 A1* | 8/2003 | Ng | 436/180 |
| 2003/0170698 A1 | 9/2003 | Gascoyne et al. | |
| 2004/0055891 A1 | 3/2004 | Pamula et al. | |
| 2005/0031657 A1 | 2/2005 | Gilson et al. | |
| 2005/0158845 A1 | 7/2005 | Wikswo et al. | |
| 2006/0078893 A1* | 4/2006 | Griffiths et al. | 435/6 |
| 2006/0254933 A1 | 11/2006 | Adachi et al. | |
| 2009/0127123 A1 | 5/2009 | Raccurt et al. | |
| 2010/0041086 A1* | 2/2010 | Pamula et al. | 435/18 |
| 2011/0104725 A1* | 5/2011 | Pamula et al. | 435/7.92 |

FOREIGN PATENT DOCUMENTS
WO     WO0218539 A2    3/2002

OTHER PUBLICATIONS

Wiederschain G., Raghavan S., Kolodny E., "Characterization of 6-hexadecanoylamino-4-methylumbelliferyl-β-D-galactopyranoside as fluorogenic substrate of galactocerebrosidase for the diagnosis of Krabbe disease", (1992) Clinica Chimica Acta, 205 (1-2), pp. 87-96.
Svennerholm, Lars et al., Clinica Chimica Acta, vol. 106, Issue 2, Sep. 25, 1980, pp. 183-193; "Assay of the β-glucosidase activity with natural labelled and artificial substrates in leukocytes from homozygotes and heterozygotes with the norrbottnian type (type 3) of Gaucher disease".
Broadhead et al., Clinica Chemica Acta, vol. 75, Issue 1, Feb. 15, 1977, pp. 155-161, "The diagnosis of gaucher's disease in liver using 4-methylumbelliferyl-β-d-glucopyranoside".
Besley G.T.N., Moss S.E., "Studies on sphingomyelinase and β-glucosidase activities in Niemann-Pick disease variants. Phosphodiesterase activities measured with natural and artificial substrates", (1983) Biochimica et Biophysica Acta—Lipids and Lipid Metabolism, 752 (1), pp. 54-64.
Boggs, Dallas E., "Detection of Inborn Errors of Metabolism", Critical Reviews in Clinical Laboratory Sciences 1971, vol. 2, No. 4 : pp. 529-572.
Jie Ding, "System level architectural optimization of semi-reconfigurable microfluidic system," M.S. Thesis, Duke University Dept of Electrical Engineering, 2000.
Yves Fouillet et al., "Digital microfluidic design and optimization of classic and new fluidic functions for lab on a chip systems," Microfluid Nanofluid, vol. 4, pp. 159-165 (2008).
Hopwood, et a., "A fluorometric assay using 4-methylumbelliferyl alpha-L-iduronide for the estimation of alpha-L-iduronidase activity and the detection of Hurler and Scheie syndromes," Clin Chim Acta. 92(2): pp. 257-265, 1979.
Moon, Hyejin, Ph.D., "Electrowetting-on-dielectric microfluidics: Modeling, physics, and MALDI application," University of California, Los Angeles, 2006.
Murphey, William H. et al., "Screening tests for argininosuccinic aciduria, orotic aciduria, and other inherited enzyme deficiencies using dried blood specimens", Biochemical Genetics, vol. 6, No. 1, pp. 51I-59, DOI: 10.1007/BF00485965, pp. 51-59, 1972.
Pollack et al., "Electrowetting-Based Actuation of Droplets for Integrated Microfluidics," Lab on a Chip (LOC), vol. 2, pp. 96-101, 2002.
Vijay Srinivasan, Vamsee K. Pamula, Richard B. Fair, "An integrated digital microfluidic lab-on-a-chip for clinical diagnostics on human physiological fluids," Lab on a Chip (LOC), vol. 4, pp. 310-315, 2004.

* cited by examiner

*Primary Examiner* — Ralph Gitomer
(74) *Attorney, Agent, or Firm* — Ward and Smith, P.A.; William A. Barrett

(57) ABSTRACT

A method of conducting a droplet-based enzymatic assay is provided. The method generally makes use of a droplet actuator. A droplet comprising an enzyme of interest is provided on the droplet actuator along with a droplet comprising a substrate which is potentially modified in the presence of the enzyme. The method involves executing droplet operations on the droplet actuator to combine the droplets, thereby yielding an assay droplet, and detecting modification of the substrate by the enzyme in the assay droplet on the droplet actuator. The enzyme of interest may, for example, be a potentially mutated or improperly folded enzyme exhibiting altered enzyme activity as compared to a corresponding normal enzyme.

39 Claims, 3 Drawing Sheets

METHOD OF CONDUCTING A DROPLET BASED ENZYMATIC ASSAY

1 RELATED PATENT APPLICATIONS

This application is a National Stage application filed under Rule 371 based on PCT/US08/57959 filed Mar. 23, 2008 which claims benefit to provisional application 60/896,341 filed Mar. 22, 2007.

2 GOVERNMENT INTEREST

This invention was made with government support under DK066956-02 and GM072155-02 awarded by the National Institutes of Health of the United States. The United States Government has certain rights in the invention.

3 BACKGROUND

Droplet actuators are used to conduct a variety of droplet operations. A droplet actuator typically includes two substrates separated by a gap. The substrates include electrodes for conducting droplet operations. The gap between the substrates is typically filled with a filler fluid that is immiscible with the fluid that is to be subjected to droplet operations. Droplet operations are controlled by electrodes associated with one or both of the substrates.

In many locations around the world, newborn infants are routinely tested for various genetic conditions. However, the tests are expensive and typically only a small fraction of possible disorders are included in the testing regimen. For example, there are at least 50 lysosomal storage diseases that are rarely tested. Some of these conditions are extremely rare. Pathologies often involve significant physical and mental debilitation leading to death. Therapies are available in some cases. Outcomes may be improved with early treatment. One such disease is Pompe's disease, which results from a deficiency in alpha-glucosidase. Enzyme replacement therapy is available for treating the condition. However, newborns are rarely screened for Pompe's.

With respect to conditions that are tested in newborn infants, testing typically involves collecting a sample of blood is removed from the heel of a baby. The sample is placed on a card, dried, and sent to a central laboratory for testing. The dried blood sample is typically about 6 millimeters (mm) in diameter. The dried blood sample is tested for an indicator of several diseases. Using current methodologies, a prohibitively large volume of blood would be required in order to do a significantly larger number of tests.

There is a need for testing methods that are highly sensitive and require only a small volume of blood. There is a need in the art for improved methods of conducting enzymatic assays using droplet actuators. There is also a need in the art for methods of conducting enzymatic assays that significantly speeds up the time from sample collection to result.

4 BRIEF DESCRIPTION OF THE INVENTION

The invention provides a method of conducting a droplet-based enzymatic assay. The method generally makes use of a droplet actuator. A droplet comprising an enzyme of interest is provided on the droplet actuator along with a droplet comprising a substrate which is potentially modified in the presence of the enzyme. The method involves executing droplet operations on the droplet actuator to combine the droplets, thereby yielding an assay droplet, and detecting modification of the substrate by the enzyme in the assay droplet on the droplet actuator. The enzyme of interest may, for example, be a potentially mutated or improperly folded enzyme exhibiting altered enzyme activity as compared to a corresponding normal enzyme.

The methods of the invention are useful for providing diagnostic information. For example, the assay may be conducted using a clinical sample from a subject (directly from the subject or processed), the sample comprising the enzyme of interest. The method may provide diagnostic information based on the activity of the enzyme of interest from the human clinical sample relative to the expected activity of a corresponding normal enzyme. The diagnostic information may comprise information diagnostically relevant to a glycogen storage disease. For example, the glycogen storage disease comprises a lysosomal storage diseases involving a defect in a glycosidase, such as a deficiency in α-glucosidase or α-galactosidase activity.

The assay may, in certain embodiments, be conducted and the diagnostic information provided at a point of sample collection. The point of sample collection may be in the presence of the subject. Clinical samples may, for example, comprise include processed or unprocessed blood, plasma, serum, tears, saliva, and/or urine. The clinical sample may be a dried or fresh blood sample. In some embodiments, a fresh blood sample is collected from the subject and immediately loaded onto a droplet actuator for conducting the assay. In one embodiment, time from collection of the blood sample to providing diagnostic information is less than about 5 hours. In another embodiment, time from collection of the blood sample to providing diagnostic information is less than about 1 hour. In another embodiment, time from collection of the blood sample to providing diagnostic information is less than about 30 minutes. In another embodiment, time from collection of the blood sample to providing diagnostic information is less than about 15 minutes. In another embodiment, time from collection of the blood sample to providing diagnostic information is less than about 5 minutes.

The sample may be a clinical sample. The clinical sample may be a human clinical sample. The clinical sample may be a non-human animal clinical sample.

The substrate may in some cases be a glycoside substrate. The substrate may be selected releases a detectable signal, such as by releasing a fluorophore, upon contact with the enzyme of interest. In some cases, two or more assays are conducted simultaneously using different detectable signals for each enzyme tested. In some cases, the substrate is a fluorophore, such as 4-methylumbelliferyl. The substrate may include a glycoside substrate which releases a fluorophore upon contact with the enzyme of interest. Examples of such substrates include those which include glucose, galactose, fucose, mannose, sialic acid, hexose, hexosamine and/or N-acetylated hexosamine. A specific example is 4-methylumbelliferyl glycoside.

In some cases, reaction contaminants associated with the substrate are reduced or eliminated prior to producing the assay droplet. One method of reducing or eliminating reaction contaminants comprises photobleaching the substrate prior to yielding the assay droplet. In some cases, the photobleaching is effected prior to providing the droplet comprising the substrate on the droplet actuator. In other cases, the photobleaching is effected after to providing the droplet comprising the substrate on the droplet actuator.

The methods of the invention may be conducted while the reagent and/or assay droplets are at least partially surrounded by a filler fluid comprising an oil. For example, the filler fluid may include a silicone oil. The filler fluid may include a surfactant. For example, the surfactant may include a nonionic low hydrophile-lipophile balanced (HLB) surfactant. For example, the HLB may be less than about 10 or less than about 5. Examples of suitable surfactants include Triton X-15; Span 85; Span 65; Span 83; Span 80; Span 60; and fluorinated surfactants. Others are described in International Patent Application No. PCT/US 06/47486, entitled "Droplet-Based Biochemistry," filed on Dec. 11, 2006.

The droplet operations may in some cases be electrode-mediated. For example, the droplet operations may be electrowetting mediated and/or dielectrophoresis mediated.

The methods of the invention may reduce time to result by reducing the required incubation time. For example, in one example, the incubation time is not longer than about 15 hours. In another example, the incubation time is not longer than about 10 hours. In another example, the incubation time is not longer than about 5 hours. In another example, the incubation time is not longer than about 1 hour. In another example, the incubation time is not longer than about 45 minutes. In another example, the incubation time is not longer than about 30 minutes. In another example, the incubation time is not longer than about 15 minutes. In another example, the incubation time is not longer than about 10 minutes. In another example, the incubation time is not longer than about 5 minutes.

5 DEFINITIONS

As used herein, the following terms have the meanings indicated.

"Activate" with reference to one or more electrodes means effecting a change in the electrical state of the one or more electrodes which results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads are described in U.S. Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads. The beads may include one or more populations of biological cells adhered thereto. In some cases, the biological cells are a substantially pure population. In other cases, the biological cells include different cell populations, e.g., cell populations which interact with one another.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Washing" with respect to washing a magnetically responsive bead means reducing the amount and/or concentration of one or more substances in contact with the magnetically responsive bead or exposed to the magnetically responsive bead from a droplet in contact with the magnetically responsive bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Other embodiments are described elsewhere herein, and still others will be immediately apparent in view of the present disclosure.

The terms "top" and "bottom" are used throughout the description with reference to the top and bottom substrates of the droplet actuator for convenience only, since the droplet actuator is functional regardless of its position in space.

When a given component, such as a layer, region or substrate, is referred to herein as being disposed or formed "on" another component, that given component can be directly on the other component or, alternatively, intervening components (for example, one or more coatings, layers, interlayers, electrodes or contacts) can also be present. It will be further understood that the terms "disposed on" and "formed on" are used interchangeably to describe how a given component is positioned or situated in relation to another component. Hence, the terms "disposed on" and "formed on" are not intended to introduce any limitations relating to particular methods of material transport, deposition, or fabrication.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

6 BRIEF DESCRIPTION OF THE DRAWINGS

7 DETAILED DESCRIPTION OF THE INVENTION

Figure 1:
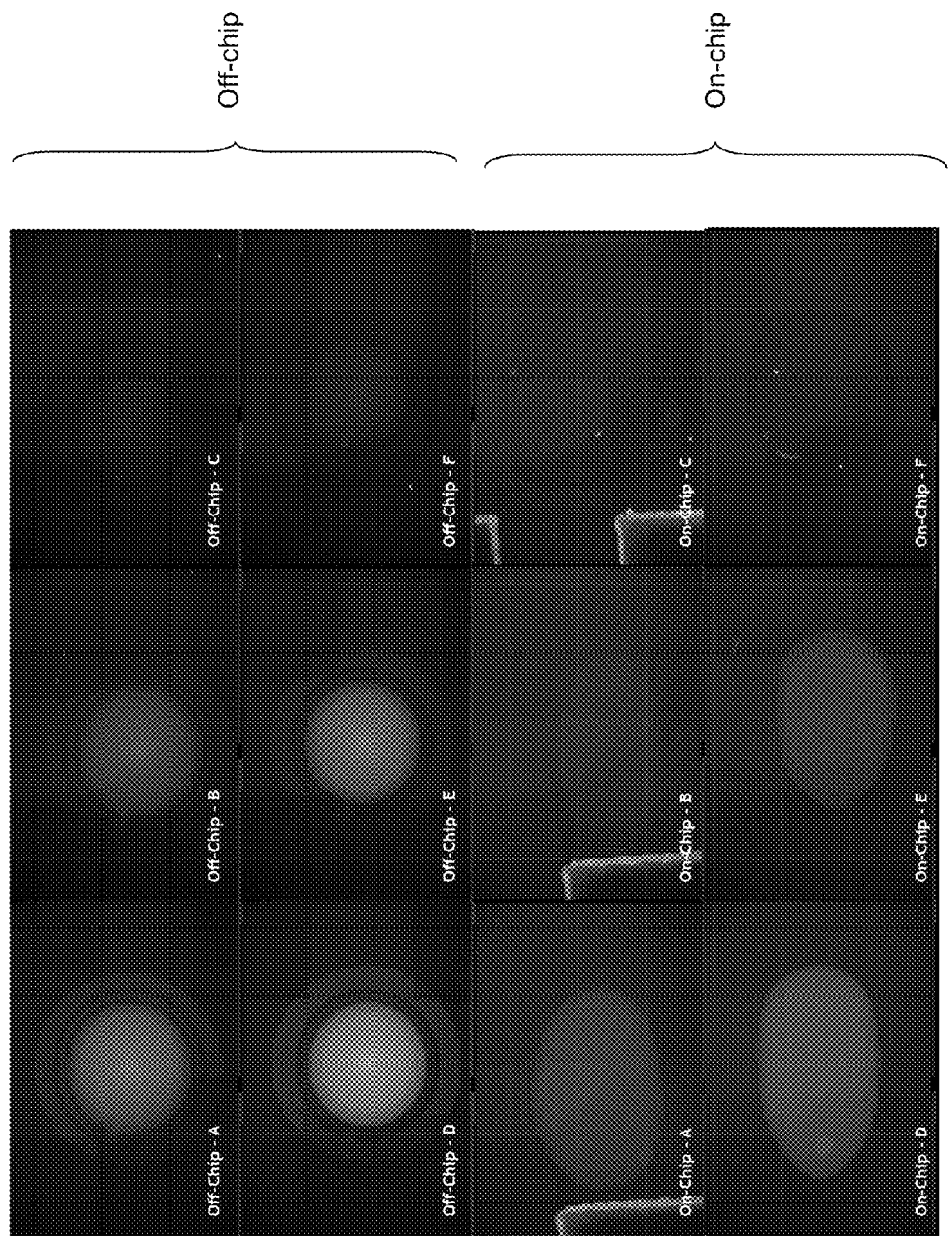
FIG. 1 illustrates the physical detection of fluorescence in Pompe assays that are conducted outside of the droplet actuator, i.e., off-chip, and in the droplet actuator, i.e., on-chip.

The invention relates to methods of conducting enzymatic assays using a droplet actuator. The enzymatic assays of the invention may have various advantages over conventional methods, such as: conducting more tests using smaller samples; conducting tests much more quickly; and/or conducting tests at the patient's bedside rather than requiring a central laboratory. The invention also relates to droplet actuators for executing the enzymatic assays of the invention and to methods of making and using such droplet actuators.

While the discussion here will focus on enzymatic assays in the context of human diagnostics, it will be appreciated that the techniques of the invention will be useful for any kind of enzymatic assay. In certain embodiment, the enzymatic assays are used for screening purposes, such as screening animals or humans for diseases. In some cases, the animals or humans being screened may be newborn animals or humans.

7.1 Enzymatic Assays on a Droplet Actuator

The enzymatic assays of the invention are accomplished using droplets. In certain embodiments, a droplet actuator is employed for conducting droplet operations. Among other things, the inventors have discovered that certain reagents required to effect enzymatic assays may be effectively manipulated on a droplet actuator in the conduct of enzymatic assays. Further, the inventors have identified droplet actuator conditions suitable for conducting droplet operations using the reagents required to effect enzymatic assays with improved results. Droplet actuators also provide the capability of analyzing single samples for multiple disease conditions and multiple samples concurrently. For example, the invention facilitates analysis of multiple conditions by enzymatic assay and/or other assay types (such as immunoassays or PCR) from a single sample on a single droplet actuator. Further, the inventors have found that droplet actuators are capable of performing sufficiently sensitive enzymatic assays using exceptionally small sample and reaction volumes. Moreover, the inventors have discovered that the tiny volumes of sample and reagent used on droplet actuators may enhance the speed of enzymatic assays, allowing them to be conducted in a fraction of the time required using conventional methods.

Among other things, the enzymatic assays of the invention facilitate diagnoses of diseases, such as diseases involving defects in enzymes. Enzymatic assays of the invention can, for example, be used to detect altered activity of a particular enzyme in a sample, which may serve as an indicator of a particular disease. Altered activity may, for example, be caused by conditions which result in the increased or reduced production of a certain enzyme or its substrate and/or conditions which result in mutant enzymes and/or substrates exhibiting increased or decreased effectiveness relative to corresponding normal enzymes and/or substrates.

Sample droplets and reagent droplets for use in conducting the enzymatic assays may be dispensed and/or combined according to appropriate assay protocols using droplet operations on a droplet actuator. Incubation of assay droplets, including temperature adjustments as needed, may also be performed on a droplet actuator. Further, detection of signals from assay droplets, such as detection of fluorescence may be conducted while the droplet is present on the droplet actuator. Further, each of these processes may be conducted while the droplet is partially or completely surrounded by a filler fluid on the droplet actuator.

In certain embodiments, certain assay steps may be conducted outside of a droplet actuator and certain assay steps may be conducted on a droplet actuator. For example, in some embodiments, sample and reagents may be combined outside the droplet actuator and the incubation and detection steps may be effected on the droplet actuator.

The enzymatic assays are generally conducted at neutral to acidic pH. The assays make use of a biological sample, such as a blood sample, or a sample derived from blood. Examples of other suitable biological samples include tears, saliva, or urine. Other biological sample types are listed in Section 8.5.

7.1.1 Droplet Operations

Droplet operations may be utilized to combine on a droplet actuator the substrate droplet with a sample droplet. The droplets are provided at an appropriate pH, and the pH may be adjusted as needed by combining the sample, substrate, and/ or sample+substrate droplets with appropriate buffer droplets. The sample+substrate droplet may then be incubated on the droplet actuator. The release of fluorophore, such as 4-methylumbelliferyl, in the droplet or the increase in fluorescence in the droplet versus time, may be measured. Multiple assays may be conducted simultaneously in a single droplet, e.g., using different fluorophores for each enzyme tested.

7.1.2 Detectable Elements

The enzymatic assays of the invention, such as glycosidase assays, make use of substrates with a detectable element. In one aspect of this embodiment, the detectable element is a fluorophore. Examples of suitable fluorophores include, be 4-methylumbelliferyl. For glycosidase assays of the invention, 4-methylumbelliferyl glycosides may be utilized as substrates for the droplet-based assays utilized herein. 4-methylumbelliferyl may be attached through an alpha or beta linkage to glucose, galactose, fucose, mannose, sialic acid, hexose, hexosamine and/or N-acetylated hexosamine. The appropriate 4-methylumbelliferyl glycoside may be used as the substrate for the appropriate enzyme. For example, 4-methylumbelliferyl α-D-glucopyranoside may be used as the substrate in an assay designed to analyze the activity of α-glucosidase in a sample, as indicator of Pompe's disease. Similarly, 4-methylumbelliferyl α-D-galactopyranoside may be used as the substrate in an assay designed to analyze the activity of α-galactosidase in a sample, as indicator of Fabry's disease.

In certain embodiments it is useful to remove contaminants form the substrate, e.g., by phtobleach the substrate, prior to the assay reaction. The inventors have found that a reaction contaminant that may be present in the 4-methylumbelliferyl preparation. The reaction contaminant extends the time required for conducting the assay. Contaminant removal, e.g., by photobleaching, appears to reduce or eliminate the impact reaction contaminant(s), resulting in reduced, preferably greatly reduced, reaction time. For example, the 4-methylumbelliferyl glycoside substrate may be photobleached prior to the assay reaction. For example, in some cases the photobleaching step decreases the reaction time from about 22 hours to about 30 minutes.

7.2 Diagnosis of Lysosomal Storage Diseases

The invention provides modified assays for detecting altered enzymatic activity on a droplet actuator. Among the enzymatic assays which may be conducted according to the methods of the invention are those methods useful in the diagnosis of lysosomal storage diseases involving defects in glycosidases. Enzymatic indicators of lysosomal storage diseases can be identified using droplet based assays on a droplet actuator. Assays of the appropriate glycosidase activity can be used to detect altered activity of a particular glycosidase, which may be an indicator of a particular lysosomal storage disease. A deficiency in α-glucosidase activity, for example, is a diagnostic indicator of Pompe's disease. Similarly, a deficiency in α-galactosidase activity is a diagnostic indicator of Fabry's disease. Multiple diseases and/or multiple samples can be tested simultaneously on a single droplet actuator.

Enzymatic assays for detecting such conditions may be accomplished in a much shorter time period as compared to assays conducted using conventional methods. For example, in certain embodiments, the incubation time required to effect diagnostically relevant results is less than about 15, 10, 5, 4, 3, 2 or 1 hours. In certain other embodiments, the incubation time required to effect diagnostically relevant results is less than about 45, 30, 15, 10, 5, 4, 3, 2 or 1 minutes. Similarly, in certain embodiments, the incubation time required to effect diagnostically relevant results for lysosomal storage diseases involving defects in glycosidases is less than about 15, 10, 5, 4, 3, 2 or 1 hours. In certain other embodiments, the incubation time required to effect diagnostically relevant results for lysosomal storage diseases involving defects in glycosidases is less than about 45, 30, 15, 10, 5, 4, 3, 2 or 1 minutes. Moreover, such enzymatic assays may be conducted in a small laboratory or on a countertop, for example in a birthing unit, or even at a point of sample collection, such as the patient's bedside.

7.2.1 Pompe's Disease

In the assay for Pompe's disease detecting α-glucosidase activity droplet operations on a droplet actuator are employed to combine a first droplet of dried blood and buffer with a second droplet including 4-methylumbelliferyl α-D-glucopyranoside to provide a reaction droplet. The reaction droplet may be provided at, and/or adjusted to, an acid and/or alkaline pH and incubated for a period of time. Typical incubation time may, for example, be between about 30 minutes and about 22 hours. When sufficient signal is generated, the reaction may be quenched by adding an alkaline droplet to the reaction droplet. The amount of fluorescence that results from the release of 4-methylumbelliferyl is measured and compared to appropriate standards.

In one example, the dried blood spot is reconstituted in about 180 micro-liters (µl) of water and added to reaction components giving a final concentration of about 1.4 mM 4-methylumbelliferyl α-D-glucopyranoside in about 0.04M NaAc pH 3.8 or pH 7.0, with or without about 5.9 uM of the inhibitor acarbose. The reaction droplet may be quenched with a droplet comprising $NaHCO_3$, pH 9.0 at a concentration of about 0.1 M for assays that are conducted on the bench, and about 0.4M for assays that are conducted in the droplet actuator.

7.2.2 Additional Remarks

In the enzymatic assays described herein, the detection of indicator occurs at end-points. In another embodiment, kinetic assays are employed and reaction times may be significantly decreased. In one embodiment of the invention, the droplet actuator may be located at a facility outside of a hospital. For example, the facility may be at a state laboratory. In one embodiment of the invention, the droplet actuator may be located within the hospital, such as within a newborn unit.

In embodiments of the invention, the blood sample to be tested may be dried. Alternatively, the blood sample to be tested is fresh and has not been dried. The embodiments described herein relate to blood; however, these embodiments are non-limiting and other embodiments are contemplated. For example, other biological samples, such as tears, saliva, or urine, may be used in the testing of certain diseases. For example, in the testing to diagnose Fabry's disease, tears may be tested. The volume of sample and reagent droplets used to conduct the enzymatic assays of the invention may in some embodiments range from about 1 nL to about 100 mL, or about 10 nL to about 10 mL, or about 1 µL to about 10 µL. In another embodiments, volume of sample and reagent droplets used to conduct the enzymatic assays of the invention may be less than about 100 µL or less than about 50 µL or less than about 25 µL.

8 EXAMPLES

The ensuing examples are illustrative of the invention and are not intended to limit the scope of invention:

8.1 Bench Assay of α-Glucosidase Activity for Detecting Pompe's Disease

Table 1 shows the results of an assay of α-glucosidase activity for detecting Pompe's disease. For example, Table 1 shows the amount of fluorescence detected under two different assay conditions. The assay is conducted outside of a droplet actuator, i.e., off-chip. The samples are assayed as described above.

TABLE 1

Assay results of α-glucosidase activity for detecting Pompe's disease (On-bench)

|  | pH 3.8 | pH 7.0 |
| --- | --- | --- |
| Blood + Substrate | 17813 | 11257 |
| Blood + Substrate + Inhibitor | 10898 | 4382 |
| Substrate + Inhibitor | 3214 | 3396 |

Referring to Table 1, the samples are incubated for about 18 hours at about 25 C. One reaction is conducted at about pH 3.8 and one reaction is conducted at about pH 7.0. The sample/reagent volume is about 2.5 µl. The reaction is quenched with about 100 µl of 0.1M NaHCO$_3$, pH 9.0. The fluorescence may be detected in a plate reader, measuring the wavelength 360Ex/460Em. As shown in Table 1, the signal increases in the presence of substrate that has blood. The signal is decreased in the presence of the acarbose inhibitor which inhibits glycosidase activity.

In one embodiment of the invention, the amount of sample that is required for the droplet actuator methods may be approximately 50% of the volume used in currently available methods of measuring Pompe's disease. For example, 180 µl of resuspended sample may be assayed in the Pompe's disease assay for analysis in a droplet actuator. For use on the droplet actuator, the dried spot may be reconstituted in a smaller volume. For example, in one embodiment, about 90 µl and about 180 µl of water may be used to increase the concentration of enzyme in the sample, which will increase assay signal and/or shorten the required assay time.

8.2 Assay of α-Glucosidase Activity to Detect Pompe's Disease, Fluorescence Detection on a Droplet Actuator Table 2 provides the results of an assay of α-glucosidase activity to detect Pompe's disease. For example, Table 2 shows the amount of fluorescence detected under two different assay conditions. The incubation and quenching were conducted outside of the droplet actuator, i.e., off-chip, and the fluorescence detection may be conducted in a droplet actuator, i.e., on-chip.

TABLE 2

Assay results of α-glucosidase activity for detecting Pompe's disease (Off-chip incubation; On-chip quench)

| A | Blood + MUG pH 3.8 | 89.8 |
| --- | --- | --- |
| B | Blood + MUG pH 3.8 + Inhibitor | 68.8 |
| C | Water + MUG pH 3.8 + Inhibitor | 62.4 |
| D | Blood + MUG pH 7.0 | 76.4 |
| E | Blood + MUG pH 7.0 + Inhibitor | 59.8 |
| F | Water + MUG pH 7.0 + Inhibitor | 39.5 |

Referring to Table 2, the reactions may be conducted in microfuge tubes, incubated for about 21.5 hours at about 25 C, and NaHCO$_3$ is added in order to quench the sample. A portion of the sample is removed for the detection of fluorescence in the droplet actuator. Under all of the assay conditions, pH 3.8, pH 7.0, and in the presence or absence of inhibitor, an increase in fluorescence is observed in the presence of blood. The amount of fluorescence in the absence of inhibitor is greater than in the presence of inhibitor. Fluorescence is indicated by RFUs (relative fluorescence units).

FIG. 1 illustrates the physical detection of fluorescence in Pompe assays that are conducted outside of the droplet actuator, i.e., off-chip, and in the droplet actuator, i.e., on-chip. Samples are reacted as described in Table 2. Samples A, B and C are reacted at pH 3.8. Samples D, E and F are reacted at pH 7.0. Samples are removed and analyzed by measuring the fluorescence on a microscope (350Ex/420Em). Panels C and F represent samples with substrate, inhibitor but no blood. Panels B and E represent samples with substrate, inhibitor and blood. Panels A and D represent samples with substrate and blood. In the on-chip sample, the incubation is off-chip for about 21.5 hours at room temperature and then the sample is mixed 1:1 on-chip with about 0.4 M bicarbonate buffer, pH 9.0 with the droplet actuator. As shown, the fluorescence increases with time in both the on-chip and off-chip samples.

Figure 2A:
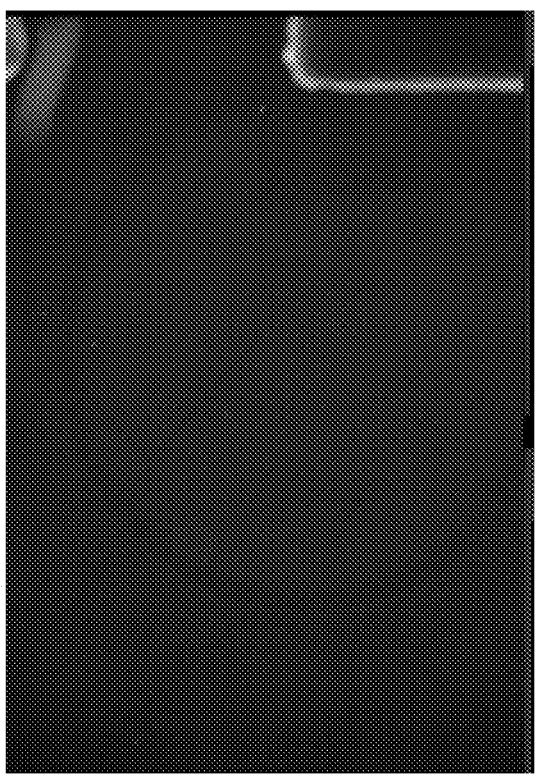
FIGS. 2A and 2B illustrate the physical detection of fluorescence in assays that are conducted substantially entirely in the droplet actuator, i.e., on-chip.
Figure 2B:

FIGS. 2A and 2B illustrate the physical detection of fluorescence in assays that are conducted substantially entirely in the droplet actuator, i.e., on-chip. The reactions are conducted as described above, and the reactions are incubated at about 25 C for about 22.5 hrs. The reactions are quenched with NaHCO$_3$, and the fluorescence may be read on a microscope (350Ex/420Em). The droplet size may be about 1 µl.

FIG. 2A shows the fluorescence detected in the presence of water, while FIG. 2B shows the fluorescence detected in the presence of blood. As illustrated in FIG. 2B, the fluorescence detected in the presence of blood is significantly increased over the minimal amount of fluorescence that is detected in the presence of water (FIG. 2A).

8.3 Comparison of On-Chip and Off-Chip Procedures

Table 3 provides a comparison of the analyses conducted in Table 1 vs. the analyses conducted in FIGS. 2A and 2B. In particular, Table 3 provides a comparison of the results from procedures conducted outside of the droplet actuator, i.e., off-chip, with procedures conducted in the droplet actuator, i.e., on-chip. As shown, the ratio of signal in the blood-containing sample to signal in the water control sample are determined for both the procedures conducted off-chip and on-chip. The ratio of signals in the off-chip sample is comparable to the ratio of signals in the on-chip sample. For diagnosis of Pompe's disease, both the off-chip and on-chip assays indicate the presence or absence of α-glucosidase activity.

TABLE 3

Off-chip vs. on-chip comparison

|  | Off-chip | On-chip |
| --- | --- | --- |
| A: Blood + Substrate pH 3.8 | 17813 | 3.39e−7 |
| B: Water + Substrate pH 3.8 | 3214 | 6.84e−8 |
| Signal increase (A/B) | 5.54 | 4.85 |

Figure 3:
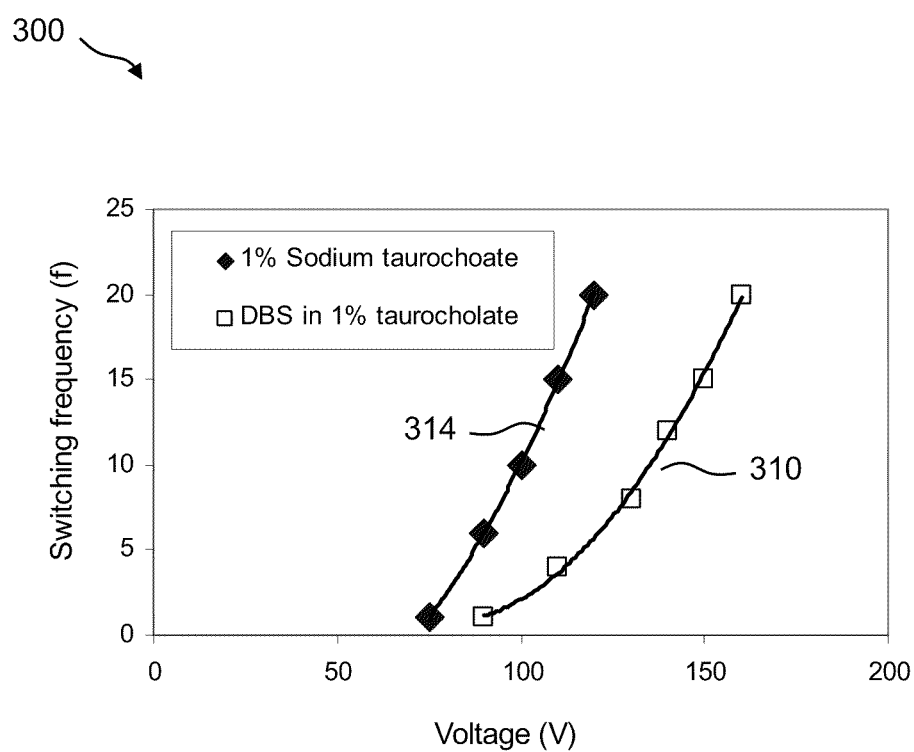
FIG. 3 illustrates a plot of an assay that measures α-galactosidase activity in a droplet actuator.

FIG. 3 illustrates a plot 300 of an assay that measures α-galactosidase activity in a droplet actuator; a defection in α-galactosidase is diagnostic of Fabry's disease. Plot 300 of FIG. 3 demonstrates that the reagents for Fabry's disease test and the reconstituted blood sample can be electrowetted. A dried blood spot may be reconstituted in about 250 µl of 1% (w/v) sodium taurocholic acid. No α-galactosidase reaction is performed. The substrate, 4-methylumbelliferyl α-galactoside is not included and enzymatic activity is not measured. The reaction is incubated for about an hour in a droplet actuator. The droplet actuator utilized a single layer glass chip, 12 um parylene C, and 1% Teflon AF (100 mm/sec withdrawal). The top substrate was ITO and 1% Teflon AF (100 mm/sec withdrawal). The reaction is conducted in the presence and absence of blood. The switching frequency (f) may be determined as a function of the applied voltage (V) for both the sample in the presence of blood, shown by a curve 310, and the sample in the absence in blood, shown by a curve 314. The results indicate that the assay to detect α-galactosidase activity is compatible with the droplet actuator.

In one embodiment of the invention, the blood sample is suspended in a buffer. In one aspect of the invention, the blood sample is resuspended in about 180 μl of buffer. Blood from one disc may, for example, be reconstituted in about 45 to about 360 μl of water. In an embodiment of the invention, a 1 mm portion of a 6 mm blood spot may be resuspended in about 180 μl of buffer. Blood from one disc may, for example, be reconstituted in about 45 to about 360 μl of water. In one aspect of the invention, the buffer may contain about 1% (w/v) sodium taurocholic acid. Aliquots of the resuspended sample may undergo a variety of assays. The various assays may be multiplexed in a droplet actuator. For example, the various assays may be conducted at various stations in a droplet actuator.

The assays described herein may be performed in a hospital, as described above. In one aspect of this embodiment, approximately 0.1 ml of blood is removed from a newborn. The 0.1 ml of blood may be used directly without dilution or reconstitution before or after removal of blood cells. The sample may be inserted in a droplet actuator for the processing of the sample and assay analysis.

8.4 Droplet Actuator

For examples of droplet actuator architectures suitable for use with the invention, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; Pollack et al., International Patent Application No. PCT/US 06/47486, entitled "Droplet-Based Biochemistry," filed on Dec. 11, 2006, the disclosures of which are incorporated herein by reference.

8.5 Fluids

For examples of sample fluids useful in the assays of the invention, see the patents listed in section 8.4, especially International Patent Application No. PCT/US 06/47486, entitled "Droplet-Based Biochemistry," filed on Dec. 11, 2006. In some embodiments, the fluid includes a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, fluidized tissues, fluidized organisms, biological swabs and biological washes.

8.6 Filler Fluids

The gap will typically be filled with a filler fluid. The filler fluid may, for example, be a low-viscosity oil, such as silicone oil. Other examples of filler fluids are provided in International Patent Application No. PCT/US 06/47486, entitled "Droplet-Based Biochemistry," filed on Dec. 11, 2006.

9 CONCLUDING REMARKS

The foregoing detailed description of embodiments refers to the accompanying drawings, which illustrate specific embodiments of the invention. Other embodiments having different structures and operations do not depart from the scope of the present invention.

This specification is divided into sections for the convenience of the reader only. Headings should not be construed as limiting of the scope of the invention.

It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A method of conducting a droplet-based enzymatic assay, the method comprising:
    (a) providing a droplet actuator;
    (b) providing on the droplet actuator:
        (i) a droplet comprising an enzyme of interest;
        (ii) a droplet comprising a substrate which is potentially modified in the presence of the enzyme;
    (c) executing droplet operations on the droplet actuator to combine the droplet of (b)(i) with the droplet of (b)(ii), thereby yielding an assay droplet, wherein the droplet operations are electrowetting mediated;
    (d) detecting modification of the substrate by the enzyme in the assay droplet on the droplet actuator; and
    wherein each of the droplet of (b)(i), the droplet of (b)(ii) and the assay droplet is at least partially surrounded by a silicone oil filler fluid comprising an nonionic low hydrophile-lipophile balanced (HLB) surfactant.

2. The method of claim 1 wherein the droplet comprising an enzyme of interest has a volume which is less than about 500 μL.

3. The method of claim 1 wherein the droplet comprising an enzyme of interest has a volume which is less than about 100 μL.

4. The method of claim 1 wherein the droplet comprising an enzyme of interest has a volume which is less than about 50 μL.

5. The method of claim 1 wherein the droplet comprising an enzyme of interest has a volume which is less than about 25 μL.

6. The method of claim 1 wherein the droplet comprising a substrate has a volume which is less than about 500 μL.

7. The method of claim 1 wherein the droplet comprising a substrate has a volume which is less than about 100 μL.

8. The method of claim 1 wherein the droplet comprising a substrate has a volume which is less than about 50 μL.

9. The method of claim 1 wherein the droplet comprising a substrate has a volume which is less than about 25 μL.

10. The method of claim 1 wherein the enzyme of interest is a potentially mutated or improperly folded enzyme exhibiting altered enzyme activity as compared to a corresponding normal enzyme.

11. The method of claim 1 wherein the substrate comprises a glycoside substrate.

12. The method of claim 1 wherein the substrate releases a detectable upon contact with the enzyme of interest.

13. The method of claim 12 wherein two or more assays are conducted simultaneously using different fluorophores for each enzyme tested.

14. The method of claim 1 wherein the substrate releases a fluorophore upon contact with the enzyme of interest.

15. The method of claim 14 wherein two or more assays are conducted simultaneously using different fluorophores for each enzyme tested.

16. The method of claim 14 wherein the fluorophore comprises 4-methylumbelliferyl.

17. The method of claim 1 wherein the substrate comprises a glycoside substrate which releases a fluorophore upon contact with the enzyme of interest.

18. The method of claim 1 wherein the substrate comprises a glycoside substrate comprising glucose, galactose, fucose, mannose, sialic acid, hexose, hexosamine and/or N-acetylated hexosamine.

19. The method of claim 17 wherein the substrate comprises a 4-methylumbelliferyl glycoside.

20. The method of claim 11 further comprising reducing or eliminating reaction contaminants associated with the substrate prior to yielding the assay droplet.

21. The method of claim 20 wherein the reducing or eliminating reaction contaminants comprises photobleaching the substrate prior to yielding the assay droplet.

22. The method of claim 21 wherein the photobleaching is effected prior to providing the droplet comprising the substrate on the droplet actuator.

23. The method of claim 21 wherein the photobleaching is effected after to providing the droplet comprising the substrate on the droplet actuator.

24. The method of claim 1 wherein the substrate comprises a 4-methylumbelliferyl glycoside substrate.

25. The method of claim 24 further comprising photobleaching the substrate prior to yielding the assay droplet.

26. The method of claim 1 wherein the HLB is less than about 10.

27. The method of claim 1 wherein the HLB is less than about 5.

28. The method of claim 1 wherein the surfactant is selected from the group consisting of octylphenol ethoxylate; sorbitan trioleate; sorbitan tristearate; sorbitan sesquioleate; sorbitan monooleate; sorbitan monostearate; and fluorinated surfactants.

29. The method of claim 1 wherein the droplet operations comprise electrode-mediated droplet operations.

30. The method of claim 1 wherein the droplet operations are dielectrophoresis mediated.

31. The method of claim 1 wherein step 1(d) is effected during and/or following an incubation period during which the assay droplet is incubated for a period not longer than about 15 hours.

32. The method of claim 1 wherein step 1(d) is effected during and/or following an incubation period during which the assay droplet is incubated for a period not longer than about 10 hours.

33. The method of claim 1 wherein step 1(d) is effected during and/or following an incubation period during which the assay droplet is incubated for a period not longer than about 5 hours.

34. The method of claim 1 wherein step 1(d) is effected during and/or following an incubation period during which the assay droplet is incubated for a period not longer than about 1 hour.

35. The method of claim 1 wherein step 1(d) is effected during and/or following an incubation period during which the assay droplet is incubated for a period not longer than about 45 minutes.

36. The method of claim 1 wherein step 1(d) is effected during and/or following an incubation period during which the assay droplet is incubated for a period not longer than about 30 minutes.

37. The method of claim 1 wherein step 1(d) is effected during and/or following an incubation period during which the assay droplet is incubated for a period not longer than about 15 minutes.

38. The method of claim 1 wherein step 1(d) is effected during and/or following an incubation period during which the assay droplet is incubated for a period not longer than about 10 minutes.

39. The method of claim 1 wherein step 1(d) is effected during and/or following an incubation period during which the assay droplet is incubated for a period not longer than about 5 minutes.

* * * * *